(12) United States Patent
Curran et al.

(10) Patent No.: US 7,197,774 B2
(45) Date of Patent: Apr. 3, 2007

(54) SUPPLIED AIR HELMET HAVING FACE SEAL WITH DIFFERENTIATED PERMEABILITY

(75) Inventors: Desmond T. Curran, Durham (GB); Peter D. Lee, Cleveland (GB); Richard D. Williams, Lancaster (GB); Peter N. Yates, Lancaster (GB); Derek S. Baker, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 333 days.

(21) Appl. No.: 10/987,512

(22) Filed: Nov. 12, 2004

(65) Prior Publication Data

US 2006/0101555 A1    May 18, 2006

(51) Int. Cl.
  *A61F 9/02* (2006.01)
  *A62B 18/08* (2006.01)
(52) U.S. Cl. .............................. 2/441; 2/171.3; 2/424; 2/414; 128/200.28; 128/201.25; 128/206.21; 128/206.24
(58) Field of Classification Search .................... 2/422, 2/442, 410, 441, 424, 414, 171.3; 128/206.24, 128/200.28, 201.22, 201.23, 201.24, 206.21, 128/201.25
  See application file for complete search history.

(56) References Cited

U.S. PATENT DOCUMENTS

| | | | |
|---|---|---|---|
| 577,926 A | 3/1897 | Miller | |
| 3,031,673 A | 5/1962 | Korolick | |
| 3,362,403 A | 1/1968 | Fleming et al. | |
| 3,562,813 A | 2/1971 | Origer | |
| 3,806,951 A | 4/1974 | Halteman | |
| 3,825,952 A | 7/1974 | Pershing et al. | |
| 3,955,570 A | 5/1976 | Hutter, III | |
| 4,019,508 A | 4/1977 | Der Estephanian et al. | |
| 4,055,173 A | 10/1977 | Knab | |
| 4,136,688 A | 1/1979 | Gorman | |
| 4,150,443 A * | 4/1979 | McNeilly ........................ 2/436 |
| 4,280,491 A * | 7/1981 | Berg et al. ............. 128/201.24 |
| 4,462,399 A | 7/1984 | Braun | |
| 4,484,575 A | 11/1984 | Brockway et al. | |
| 4,561,162 A | 12/1985 | Brockway et al. | |
| 4,573,217 A | 3/1986 | Reed | |
| 4,586,500 A | 5/1986 | Glynn | |
| 4,676,236 A * | 6/1987 | Piorkowski et al. ... 128/201.23 |

(Continued)

FOREIGN PATENT DOCUMENTS

| | | |
|---|---|---|
| AU | 133568 | 7/1947 |
| EP | 0 470 791 A2 | 2/1992 |
| EP | 1061822 B1 | 4/2003 |
| GB | 1402287 | 8/1975 |
| GB | 2310585 A | 9/1997 |
| WO | WO 99/26502 | 6/1999 |

OTHER PUBLICATIONS

Product literature for Racal Health & Safety Powered Respirators (prior art).

(Continued)

*Primary Examiner*—Rodney Lindsey
(74) *Attorney, Agent, or Firm*—Karl G. Hanson (57) ABSTRACT

A supplied air helmet 10 comprises a visor 14 and a face seal 12 that is secured to the visor. The face seal 12 includes a sealing member 18 and a frame member 16. The sealing member 18 extends radially inward from the frame member 16 and has first and second regions of permeability 20 and 22. The second region 22 has greater permeability than the first region 20. The use of a face seal 12 that has differentiated permeability allows for a controlled flow of air through the interior of the supplied air helmet 10.

18 Claims, 5 Drawing Sheets

U.S. PATENT DOCUMENTS

| | | | |
|---|---|---|---|
| 4,683,880 A | | 8/1987 | Werjefelt |
| 4,901,716 A | | 2/1990 | Stackhouse et al. |
| 4,965,887 A | | 10/1990 | Paoluccio et al. |
| 5,054,479 A | | 10/1991 | Yelland et al. |
| 5,104,430 A | | 4/1992 | Her-Mou |
| 5,125,402 A | | 6/1992 | Greenough |
| 5,394,568 A | | 3/1995 | Brostrom et al. |
| 5,410,757 A | * | 5/1995 | Vienamo et al. ............ 2/9 |
| 5,481,763 A | | 1/1996 | Brostrom et al. |
| 5,533,500 A | | 7/1996 | Her-Mou |
| 5,575,278 A | | 11/1996 | Bonhomme et al. |
| 6,014,971 A | | 1/2000 | Danisch et al. |
| 6,016,805 A | | 1/2000 | Burns et al. |
| 6,062,222 A | * | 5/2000 | Lewis et al. ........... 128/207.11 |
| 6,250,299 B1 | | 6/2001 | Danisch et al. |
| 6,478,025 B1 | | 11/2002 | Yort et al. |
| 6,704,944 B2 | * | 3/2004 | Kawainshi et al. ............ 2/436 |

OTHER PUBLICATIONS

Picture of 9000 Speedglas Helmet by 3M (prior art).
Picture of Breathe Easy™ 17 Welding Head Top by 3M (prior art).
Picture of Welding Head Top #HT-607 by 3M (prior art).
Picture of Performa A-VL Face Shield by North Safety Products (prior art).
Picture of Performa A-VL Face Seal by North Safety Products (prior art).
Picture of Prota Shell Baby Welding Shield by North Safety Products (prior art).
Picture of Air Supply Visor by Pulsafe (prior art).
Picture of Air Visor Series Welding Kit by Willson (prior art).
U.S. Appl. No. 10/987,512 to Curran et al. filed Nov. 12, 2004 entitled *Supplied Air Helmet Having Face Seal With Differentiated Permeability*.
U.S. Appl. No. 10/988,789 to Lee et al. filed Nov. 15, 2004 entitled *Frictionally Engaged Supplied Air Helmet Face Seal*.

* cited by examiner

SUPPLIED AIR HELMET HAVING FACE SEAL WITH DIFFERENTIATED PERMEABILITY

The present invention pertains to a supplied air helmet that has a face seal that exhibits differentiated airflow permeability in at least two different zones.

BACKGROUND

Supplied air helmets are regularly worn in environments where the surrounding air contains contaminants. These helmets have a fluid impermeable visor that is located in front of the wearer's face when the helmet is worn. The visor has a window that allows the wearer to see the surrounding environment. A face seal is attached to the visor to separate a breathing zone or an interior gas space from the surrounding exterior gas space. The interior gas space is located between the visor and the wearer's face and is defined, for the most part, by the face seal that is attached to the visor, the visor body, and the wearer's face. U.S. Pat. Nos. 6,014,971, 4,462,399, and 4,280,491 disclose examples of supplied air helmets that use face seals for this purpose.

Clean air is forced into the interior gas space from a supply tank or from a powered air source that drives ambient air through an air filter. The wearer breathes this clean air and exhales it back into the breathing zone. This exhaled air, along with excess clean air that is forced into the breathing zone, exits the interior gas space through openings in the face seal. The positive pressure that generally occurs within the interior gas space precludes contaminants from entering the interior gas space through the openings. Welders, for example, often use supplied air helmets as protection from breathing contaminants generated during welding procedures. Examples of welding helmets are shown in the following patent documents: U.S. Pat. Nos. 6,557,174, 6,591,424, 6,185,739, 5,533,206, 5,191,468, 5,140,707, 4,875,235, 4,853,973, 4,774,723, 4,011,594 and Des. 398,421; and WO 00/59421 and WO 99/26502.

A variety of face seal constructions have been designed for providing a separation barrier between the interior gas space and the exterior gas space and for enabling the excess air within the interior gas space to be purged to the exterior gas space. U.S. Pat. No. 4,136,688, for example, describes using a row of bristles as a face seal material. In U.S. Pat. Nos. 5,533,500 and 5,104,432, check valves are mounted on a soft face seal pad to exhaust air from the mask interior. Some supplied air helmets have used Tyvek™ or Sontara™ from DuPont as the face seal material—see U.S. Pat. No. 6,250,299 B1 to Danisch et al. and U.S. Pat. No. 6,016,805 to Burns et al., respectively. Others have used a foam material—see U.S. Pat. No. 5,054,479. Some commercially available products have used a PVC coated fabric as the face seal. These products also have incorporated an elastic material around the edge of the face seal to enable it to conform to different shaped faces. Other commercially available products, such as the Performa A-VL face shield (available from North Safety Products of Middelburg, Netherlands), have used a woven fabric for the face seal. The woven fabric has had a ruffled free edge that extends radially inward from the visor to contact the wearer's face.

While known face seal products have provided a variety of constructions for establishing a boundary between the interior gas space and the surrounding environment, these known products have not been fashioned to enable air to be purged from the mask interior in a differentiated manner. The known products thus may not have fully optimized air flow within the supplied air helmet to improve comfort and to preclude air inflow from the surrounding environment.

SUMMARY OF THE INVENTION

The present invention addresses a need for face seal that can manage air flow within the interior gas space while protecting the wearer from contaminant inflow. In brief summary, the present invention provides a supplied air helmet that comprises a visor and a face seal where the face seal is secured to the visor and includes a sealing member. The sealing member extends therefrom radially inward and has at least first and second regions of permeability, wherein the first region has greater permeability than the second region.

The inventive supplied air helmet is beneficial in that use of a face seal with differentiated permeability may provide a controlled flow of air within the interior gas space. Airflow can be managed, for example, to allow it to flow from an inlet port located at the wearer's forehead, across the front of the wearer's face, and then exit the interior gas space beneath the chin. Air that exits the interior gas space can readily enter the exterior gas space to allow room for new clean air to be furnished to the breathing zone. The managed airflow may provide a comfortable environment to the wearer and may also provide less opportunity for the wearer to inhale contaminants that may be present in the ambient environment or exterior gas space.

These and other advantages of the invention are more fully shown and described in the drawings and detailed description of this invention, where like reference numerals are used to represent similar parts. It is to be understood, however, that the drawings and description are for illustration purposes only and should not be read in a manner that would unduly limit the scope of this invention.

GLOSSARY

The terms set forth below will have the meanings as defined:

"breathing zone" means an interior gas space or a portion of the interior gas space where oxygen is inhaled by a wearer of a supplied air helmet;

"clean air" means air that has been filtered or that otherwise has been made safe to breathe;

"differentiated" means different;

"elastic" means the ability of a strained yarn to substantially recover its original size and shape immediately after being stressed to at least about twice its original length;

"exterior gas space" means the ambient atmospheric gas space that surrounds the exterior of a supplied air helmet when worn on a person;

"face" means the area on the front of a person's head, defined mainly by the cheeks and temporal area (or side portions of the facial region), chin, forehead, and facial area located therebetween;

"face seal" means a structure that contacts a person's face to help separate an interior gas space of a supplied air helmet from an exterior gas space;

"filtered air" means air that has been passed through a filter material to reduce the amount of any contaminants that may have been present in the air before it was filtered;

"frame member" means a structural part(s) that plays a role in supporting a sealing member;

"frictionally" means through use of friction;

"frictional engagement" means that the engagement occurs as a result of friction between the two parts intending to be joined without need for additional fastening from elements such as pegs, clips, and/or hook and loop materials;

"helmet" means a device that is worn on a person's head for safety or protection purposes;

"interior gas space" means the space that exists between a visor, a face seal, and a person's face when a supplied air helmet is being worn;

"knitted" means that the fabric is formed predominantly from a series of interlocked or interlocking loops that do not generally intersect each other perpendicularly in an over-and-under fashion;

"permeability" means the ability of a gaseous fluid to pass therethrough (media that has a greater permeability allows the gaseous fluid to pass therethrough more easily (i.e., with less pressure drop or greater airflow rate));

"porous" means having fluid permeability sufficient to enable air in an interior gas space of a supplied air helmet to be purged or exhausted from that space to enter an exterior gas space while under pressure from an air or oxygen supply source;

"sealing member" means a structure or combination of parts that conformably contacts a person's face to assist in defining a separation between an interior gas space and an exterior gas space;

"supplied air helmet" means a helmet that receives a supply of clean air for a wearer of the device to breathe;

"visor" means a structure that is located in front of a person's face when worn and that has a window to allow the person to see through it;

"welding helmet" means a helmet that has a darkened or darkening window;

"yarn" means a continuous strand of textile fiber(s), filament(s) or material in a form suitable for knitting; and "zone" when used in the context of the first and second zones of the sealing member means a portion of the total area of the sealing member.

DETAILED DESCRIPTION OF THE PREFERRED EMBODIMENTS

In describing preferred embodiments of the invention, specific terminology is used for the sake of clarity. The invention, however, is not intended to be limited to the specific terms so selected, and it is to be understood that each term so selected includes all the technical equivalents that operate similarly.

In the practice of the present invention, a new supplied air helmet is provided, which helmet comprises a visor and a face seal where the face seal is secured to the visor and includes a sealing member and a frame member. The sealing member extends radially inward from the frame member and has first and second regions of permeability. The second region has a greater permeability than the first region. The differentiated permeability may allow for managed airflow through the interior gas space and the sealing member.

Figures 1, 2, 3:
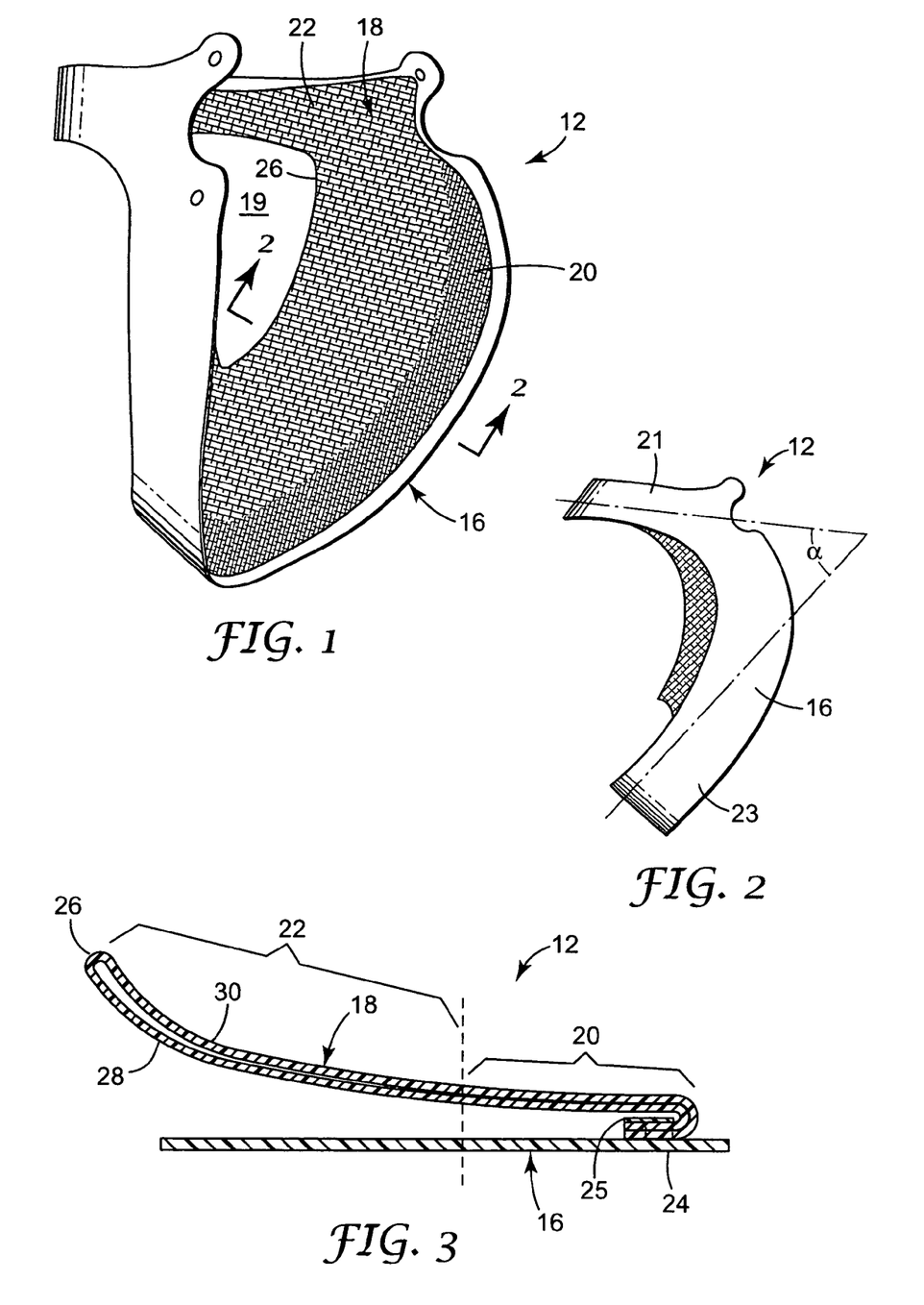
FIG. 1 is a rear perspective view of a face seal 12 in accordance with the present invention.
FIG. 2 is a left side view of the face seal 12 shown in FIG. 1.
FIG. 3 is a cross-sectional view of the face seal 12, taken along lines 2—2 of FIG. 1.

FIG. 1 illustrates a face seal 12 that comprises a frame member 16 and a sealing member 18. The frame member 16 is made from a non-porous, or fluid impermeable, material such as a thin solid plastic. The frame member 16 provides structural integrity to the face seal 12 and can be constructed such that it can be manually manipulated into position on the visor 14 (FIG. 4) in response to a force or pressure from a person's hands. The frame member 16 generally returns to its original configuration when the manual pressure is removed. Thus, the frame member 16 is desirably flexible or manually conformable while still exhibiting sufficient structural properties to enable it to retain its desired sealing configuration when in use. The frame member may be made of, for example, a 0.5 to 1.5 mm thick plastic such as polypropylene. The frame member desirably has a matted surface on at least one side to avoid reflection that could interfere with the user's vision. In general, the plastic frame may be about 0.2 mm to 5 mm thick. The frame member can be constructed as a part separate from the visor, as shown in FIG. 1, or it can alternatively be produced integral to the visor body. As the term is used in this document, "integral" means that the frame member is produced at the same time as the visor body and is not a part that is separately produced or is subsequently joined to the visor as is the frame member 16 shown in FIG. 1. An integral frame member may be constructed such that it is "one-and-the-same" with the visor body so as to be unnoticeable, or it could be a projecting flange or ridge that integrally extends from the visor body. A non-integral frame member is preferred so that the face seal can be easily replaced.

FIG. 1 further shows that the sealing member 18 extends radially inward from the frame member and that it has an opening 19 to accommodate a person's face. The opening 19 is defined by the peripheral edge 26 of the sealing member 18, which peripheral edge 26 is preferably stretchable and is preferably sized to be smaller than the wearer's face to enable the face seal to fit snugly against the various sized faces. The sealing member 18 may be made from a fabric that has elastic properties so that it can return to its original configuration after being stretched and so that it can fit various sized faces. The stretchable or elastic properties thus can enable the fabric to make adequate contact with many persons' faces when the supplied air helmet is worn.

The fabric may be porous in at least some regions to allow excess fluid within the interior gas space to pass therethrough relatively unrestrained so that air that enters the breathing zone can be exhausted into the environment to make way for new clean air that is forced into the breathing zone from an air supply source. In a supplied air system, the air pressure within the interior gas space is generally greater than the air pressure in the exterior gas space. This increased pressure causes the air to be forced out of the interior gas space. The continuous forced influx of clean air into the interior gas space creates the increased pressure. The air flow can exit the interior gas space through the pores that may be present in the fabric.

To provide improved comfort to the wearer, the porous fabric can be made from a knit that feels good when in contact with a wearer's face. Knitted fabrics are generally inherently or integrally porous and this can allow air to escape from the interior gas space through their relatively open-work weave. The knit is achieved by weaving one or more yarns in such a fashion that a series of interlocked or interlocking loops are created within the weave. A knitted fabric is distinguished from a purely woven fabric where the yarn(s) go over-and-under yarns that run approximately ninety degrees or perpendicular to them. Knitted fabrics generally comprise or consist essentially of a series of interlocking loops of one or more yarns, and the knit does not consistently occur in a perpendicular pattern. This construction can make knitted fabrics inherently more flexible than purely woven fabrics, a feature that aids comfort and fit to the face when used in a face seal.

The knitted portion of the sealing member may comprise, for example, a blend of elastic yarn, flame-retardant yarn, and comfort yarns. The elastic yarn is used to improve the fabric's "stretchability", the flame-retardant yarn functions to make the sealing member resist burning or deterioration from excess heat, and the comfort yarn improves the "feel" of the sealing member against a person's face. Threads of these yarns also may be combined to produce a yarn that has a combination of these properties such as flame retardancy and comfort in the same yarn. As indicated, the stretchability feature allows the sealing member to achieve a snug fit against various sized faces. The elastic yarn may be made predominantly from a polymer such as polyurethane or may be, for example, a modified acrylic, a latex, or a combination thereof. Commercially available products include Lycra™ (available from the DuPont Corporation of Wilmington, Del.), and Spandex™ (available from Invista Inc, of Wichita, Kans.). The flame-retardant feature is important in applications such as welding and grinding where the face seal can come into contact with sparks or drops of hot molten metal. The flame-retardant yarn may be made from a material that is inherently flame retardant, or it may be treated, for example, chemically, to impart flame retardance to the fabric. An inherently flame-retardant material is generally preferred because it may have better wash durability. Examples of flame-retardant yarns include oxidized thermally stabilized polycarylonitriles, flame-retardant polyester, and some nylons. Commercially available products include Panox™ (available from Lantor Universal Carbon Fibres of Cleckheaton, UK), Nomex™ (available from the Du Pont Corporation), and Trevira™ (available from Trevira GmbH of Bobingen, Germany). The comfort yarn assists in furnishing the fabric with a feel that is soft to touch, thus making the fabric comfortable when in contact with a person's face. An example of a comfort yarn that may be used in the inventive face seal is cotton. Other suitable comfort yarns include polyester, acrylic, rayon, and wool. The elastic, flame-retardant, and comfort yarns may generally be used in the fabric at about 0 to 20%, 30 to 100%, and 0 to 70%, respectively, based on the weight of the fabric. Preferably, the elastic, flame-retardant and comfort yarns are used at about 1 to 10%, 35 to 70%, and 30 to 60%, respectively.

The fabric further can be essentially any color and can be made from dyed polymeric materials such as polyester, modified acrylic, or a mixture or blend of these materials or threads with dyed natural yarns such as cotton. With respect to yarn diameter, the fabric could have a thickness of a single $1/50$ (fifties) count yarn or from about $1/70$ to $1/10$ count, preferably $1/60$ to $1/30$ count yarn (a $1/70$ count is thinner than a $1/10$), although other thicknesses may be suitably used. The fabric (in a non-folded combination, that is, one knitted layer) could be about 0.3 to 3 millimeters (mm) thick, preferably 0.7 to 1.5 mm thick, although greater or lesser thicknesses could be used, provided the face seal allowed for adequate fluid flow. The knitted face seal may be made from 1 to 10 yarn ends, preferably about 1 to 5 yarn ends. The number of yarn ends pertains to the number of yarn threads that are knitted together. The knitted fabric may be made such that there are about 1 gg to 20 gg, more preferably 12 gg to 18 gg. The notation "gg" pertains to the number of loops per inch. In a 16 gg machine, there are 16 needles per inch on the knitting machine. What is important is that the face seal is comfortable to wear and that it allows exhausted air to be rapidly purged from the interior gas space.

The knitted fabric may comprise approximately 15% Lycra™ an elastic yarn and approximately 85% Notex™ yarn (an inherently flame-retardant yarn). The Lycra™ adds elasticity to the inherently stretchy knitted Notex™, thereby avoiding the need for additional elastic materials on the face seal. Alternatively, the knitted material may comprise approximately 0 to 20% elastic yarn, 45 to 55% Kanecaron™ yarn (an inherently flame-retardant modified acrylic yarn obtainable from Kaneka Corporation, Tokyo, Japan), and approximately 40 to 60% cotton yarn based on weight. The elastomer may be, for example, a modified acrylic, a latex or a combination thereof. Using such knitted materials, a comfortable breathable face seal can be achieved, which allows air to properly exit the breathing zone or interior gas space of the helmet. Further description of a knitted sealing member may be found in copending patent application U.S. Ser. No. 10/987,641, entitled *Supplied Air Helmet Having A Knitted Face Seal*, filed on the same day as this patent application.

As shown in FIG. 1, the face seal 12 may have first and second zones of permeability 20 and 22, respectively. The first permeability zone 20 may have a greater resistance to airflow so that air that exits the interior gas space is more readily channeled through the second permeability zone 22. In the embodiment shown in FIG. 1, much of zone 22 will press tightly against the forehead and sides of the wearer's face, thus precluding fluid from exiting the interior gas space at those locations. Underneath the chin, however, fluid can be more rapidly purged from the mask interior. As indicated, the benefit of having such differentiated permeability is that it allows fluid to flow across the interior side of the visor lens 69 (FIGS. 4 and 5) and that it directs the flow in front of the wearer's face and under their chin to keep the wearer cool and to help prevent contaminant backflow into the interior gas space.

FIG. 2 is a side view that illustrates how the frame member 16 is constructed to define an angle α. The frame member 16 has a brow portion 21 and a chin portion 23, which portions 21 and 23 define an included angle a that is less than 90°, preferably about 50 to 80 degrees. Use of a frame member 16 that has such an angle α can allow a good fit to be achieved for prohibiting contaminant entry into the interior gas space.

FIG. 3 shows how the sealing member 18 can be secured to the frame member 16. This may be accomplished, for example, by sewing the knitted sealing member 18 to the frame member 16 at location 24. A strip of elastic material 25 may be used to help secure the fabric 18 to the frame member 16. Because the fabric is generally porous, the elastic material 25 serves to preclude the stitching yarn from tearing the fabric when sewn to the frame member. Further, the fabric 18 preferably is knitted and has elastic qualities and is applied to the frame member in a stretched or extended condition. Securement of the frame member 16 in this manner enables the fabric 18 to reside thereon in a taut condition. This pre-stretched or taut condition in turn allows the fabric 18 to snugly engage the wearer's face, particularly in the area near the peripheral inward edge 26. Although the fabric 18 may be disposed on the frame member in a prestretched condition, it does not necessarily have to be 100% stretched (typically installed at about 40 to 90% of its fully stretched condition), and thus is capable of being further stretched or expanded to snugly engage or accommodate various sized faces. In addition to sewing, the knitted fabric also may be secured to the frame member 16 using other mechanical or physical methods such as riveting, screwing, adhesive bonding, and the like.

The sealing member 18, as shown in FIG. 3, preferably is folded over to define an interior periphery 26. Use of a folded end or edge along the interior periphery 26 may further improve wearer comfort by eliminating or reducing a rough or more prominent edge that could otherwise exist. A knitted fabric that has a fold where the seal member periphery 26 makes predominant contact with the wearer's face has been found to be particularly comfortable. Opportunities for fraying also may be further reduced through use of a folded edge 26, which folded configuration could also benefit wearer comfort. Thus, the fold 26 causes the face seal to not have a free or straight edge that could roughly contact a person's face. The fold 26 further creates first and second juxtaposed layers 28 and 30. The double layered sealing member 18 may assist in preventing contaminants from entering the interior gas space. Layer 30 would reside in direct contact with the wearer's face mask when the face shield 10 is worn.

Figure 4:
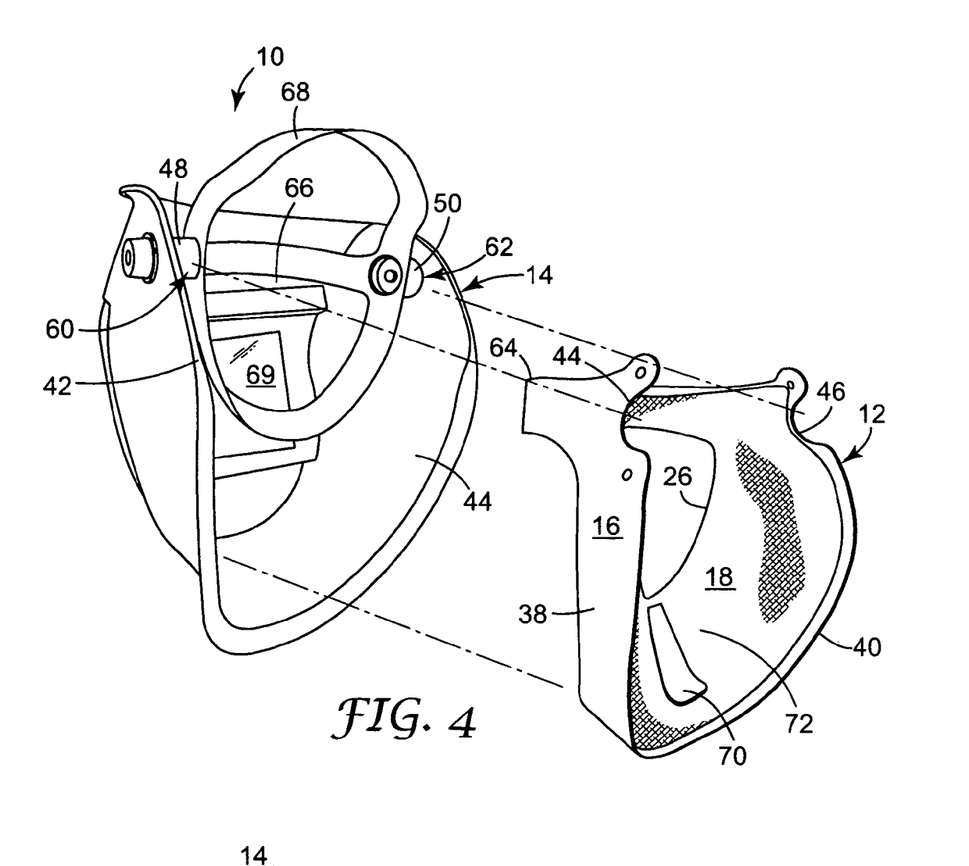
FIG. 4 is a rear perspective view of a supplied air helmet 10 in accordance with the present invention, illustrating the face seal 12 displaced from the visor 14.

FIG. 4 shows how the face seal 12 can be secured to the visor 14. The frame member 16 of the face seal 12 has first and second side portions 38 and 40. These side portions 38 and 40 can be pushed centrally inward or towards each other so that they can be squeezed between respective first and second side portions 42 and 44 of the visor 14. As indicated, the frame member 16 can be adapted to conform in response to manual pressure and to return towards an original configuration when that pressure ceases. The frame member 16 thus may be flexible or conformable to allow for its frictional placement within the more rigid visor 14. The frame member 16 has first and second receptacles 44 and 46, respectively, that are fashioned to reside against the spacer elements 48 and 50 at temporal locations 60 and 62. Once the frame member 16 is placed within the visor 14 such that receptacles 44 and 46 are juxtaposed against the hinge assembly at locations 60 and 62, the frame assembly 16 may be rotated counterclockwise until the front portion 64 of frame member 16 engages a third engagement point or shelf 66 on visor 14. When the front portion 64 of the frame member 16 is juxtaposed upon shelf 66, further rotational movement is prohibited and the face seal 12 remains statically held within the face shield 14. Although the present drawings illustrate three frictional engagement points, the invention contemplates the use of further engagement points (e.g., 4, 5, 6 or more) if necessary or desirable. Alternatively, the frame may be attached to the shield using pegs and holes as is known in the art.

An example of a face seal that can frictionally engage a helmet visor is described in detail in U.S. patent application Ser. No. 10/988,789, entitled *Frictionally Engaged Supplied Air Helmet Face Seal*, filed on the same day as this application. This face seal is particularly beneficial in that it can be attached to the visor through use of frictional engagement without additional fastening equipment. Another example of a face seal that could possibly be used is shown in U.S. Pat. No. 6,016,805 to Burns et al.

To don the helmet 10, the wearer places the crown member 68 on their cranium and rotates the visor 14 downwardly such that it resides directly in front of the wearer's face. The wearer can then look through window 69. If the helmet is used for welding purposes, the window can be an auto-darkening lens (ADL) that darkens immediately in response to light from a welder's torch (see, for example, U.S. Pat. Nos. 6,097,451 and 5,825,441, issued to Hörnell and Palmer). The wearer then pulls on tab 70 to draw the chin portion 72 of sealing member 18 underneath their chin. The remainder of the sealing member periphery 26 draws tightly against the wearer's forehead and cheek regions. A breathing zone or interior gas space is thus created, defined by the wearer's face, the sealing member 18, and the face shield or visor 14.

As indicated, the sealing member may be integrally porous to allow air to be purged from the interior gas space when under pressure. Despite the generally porous nature of the preferred knitted fabric, contaminants are precluded from entering the interior gas space because of the positive pressure that generally exists within the face seal. In operation, clean air can be supplied to the interior gas space under pressure from a powered air supply source. When using a powered air supply source, the air is powered or forced through an air filter before being directed into the interior gas space. These systems are commonly referred to as "powered air purifying respirators" or PAPRs. The air filter may be contained in a housing that is supported on a belt that is worn about the wearer's waist. Examples of these types of devices are shown in U.S. Pat. Nos. 6,279,572B1, 6,250,299B1, 6,014,971, 5,125,402, 4,965,887, 4,462,399, and 4,280,491. Examples of blowers that may be used in connection with a supplied air system for directing air into the interior gas space are shown in U.S. Pat. No. 6,575,165B1 and D449,099S. A flow sensor may be used on the supplied air helmet to provide an indication of when air flow into the breathing zone falls below a safe level—see U.S. Pat. No. 6,615,828 B1 to Petherbridge. In addition, a non-volatile memory device may be attached to the filter element to keep a record of the filter element's usage—see U.S. Pat. No. 6,186,140 B1 to Hogue.

Figure 5:
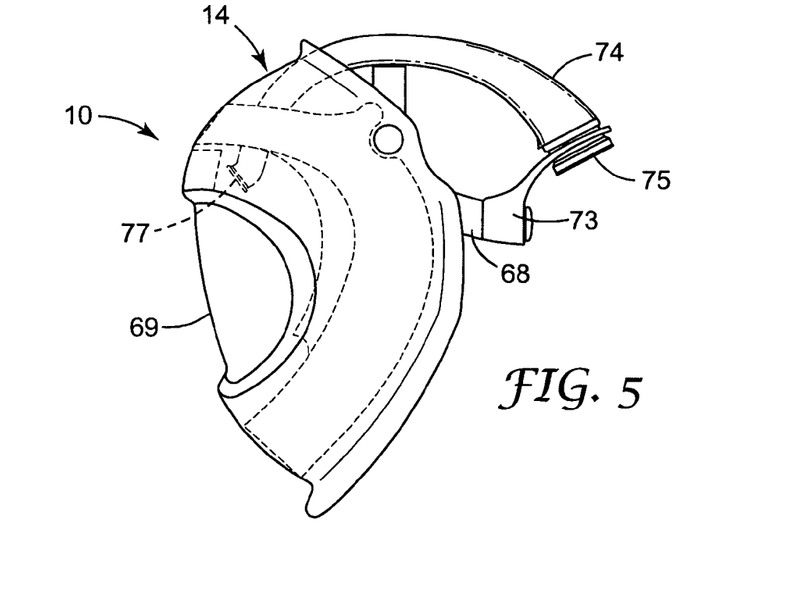
FIG. 5 is a left side view of a supplied air helmet 10, having an air duct 74, in accordance with the present invention.

As shown in FIG. 5, the air may be channeled into the interior gas space via an air duct 74 that is in fluid communication with the powered air supply source. The duct 74 has an inlet port 75 and an outlet port 77 and is supported by the crown member 68. An air duct that could be used to direct air into the interior gas space of the helmet is further shown in U.S. patent application Ser. No. 29/202,969, filed on Apr. 7, 2004 and entitled *Air Duct*, now U.S. Pat. No. D529,606 to Hind et al. The inlet 75 is connected to the clean air source, and the outlet 77 is disposed between the sealing member 18 and the wearer's forehead (not shown). As indicated, air flow exits the interior gas space through, for example, pores that may be present in the sealing member 18 (FIGS. 1 and 2). The air duct 74 can be fixed to the crown member 68 in two places. The rear of the air duct 74 can be held a fixed distance from the back of the crown member 68 by a stamped out plastic part 73. The front of the air duct 74 can be stapled to the front of the crown member 68 at the brow. In this way, the air duct 74 is prevented from moving or wobbling when in use. At the brow, the air duct 74 passes between the face seal 12 and the crown member 68. An elastomeric face seal material can allow the face seal to form a good seal around the air duct. The inlet can be connected to the clean air source, and the outlet can be disposed between the face seal and the visor. An adjustment knob can be located at the rear of the harness to adjust the circumference of the crown member to fit the wearer's head.

Figure 6:
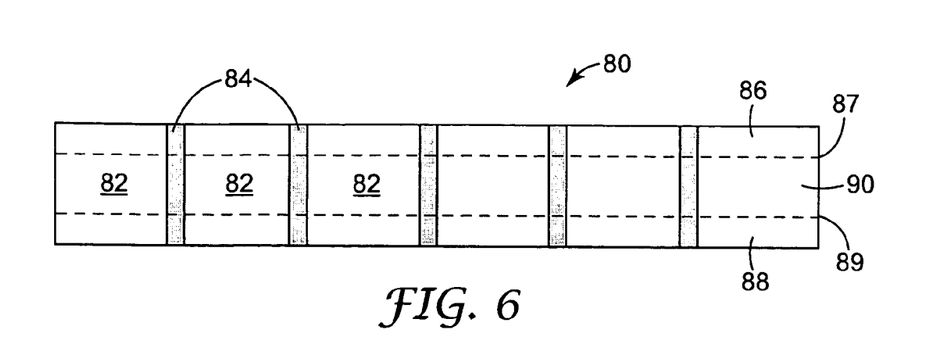
FIG. 6 is a plan view of a knitted fabric 80 that may be used to form a series of blanks 82, which blanks 82 in turn may be used to form a sealing member 18 (FIGS. 1 and 3) for a face seal.

FIG. 6 shows an elongated strip of knitted material 80, which strip 80 includes a series of blank segments 82 for forming multiple knitted sealing members. Each segment 82 is separated by a decomposable portion 84. Both segments 82 and 84 are knitted together such that the strip of material forms a continuously-knitted elongated sheet 80. The sheet 80 may have a uniform knit throughout, but it preferably includes zones that have different degrees of elasticity. Zones 86 and 88 located above and below the dashed lines 87 and 89, respectively, preferably have little or no elastic material in the weave. Zone 90, has relatively more elastic material in it than zones 86 and 88. Using a knitted material with variable zones of elasticity is beneficial to the final product's construction as discussed above with the reference to FIGS. 1 and 2. Preferably zones 86 and 88 contain about 0 to 5% elastic yarn, more preferably about 0 to 1%, and zone 90 contains about 2 to 10% elastic yarn, more preferably about 3 to 7%, based on the fabric weight.

In preparing a knitted face seal in accordance with the present invention, the elongated strip of knitted material 80 may be exposed to steam, which causes spaced zones 84 to decompose. These decomposable portions 84 may be made predominantly from a water-soluble or "seaweed" derived or man-made yarn, such as Grilon™ available from EMS-Chimie AG of Switzerland. Upon exposure to a sufficient amount of steam, the water-soluble yarn decomposes, and the elongated sheet 80 forms a series of blanks 82.

Figure 7:
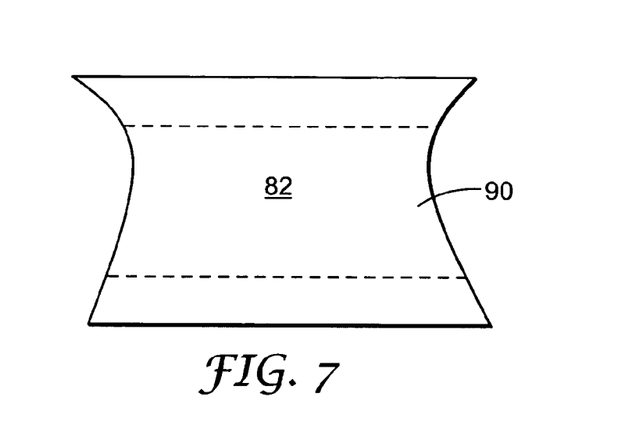
FIG. 7 is a front view of a segment 82 that has been created from the knitted fabric 80 shown in FIG. 6.

FIG. 7 shows one of the formed blanks 82. As shown, the segment 82 is "waisted". This waisted effect occurs because there is a larger amount of elastic in the central zone 90. When the sheet material 80 (FIG. 6) is exposed to steam to separate the segments 82 (FIG. 6), the elastic material may become cured, causing it to "bunch up" and causing the segments 82 to become waisted.

Figure 8:
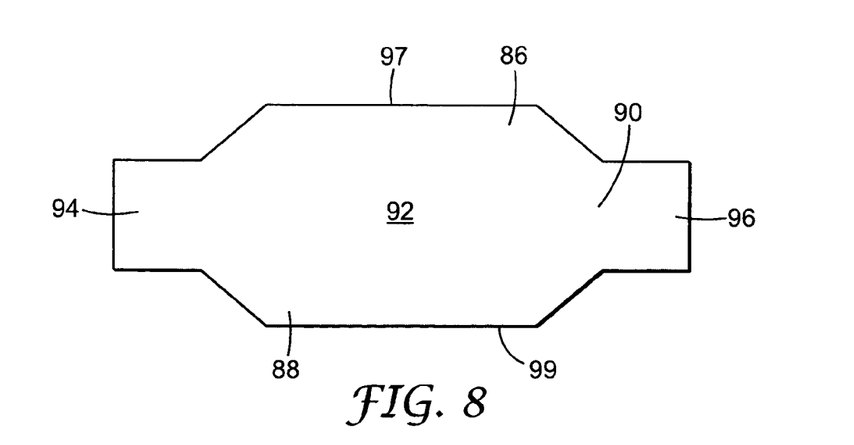
FIG. 8 is a front view of a sealing member blank 92 having a configuration that may be used to form a sealing member 18 (FIGS. 1 and 3) for attachment to a face seal frame 16 (FIGS. 1 and 3)

The waisted segments 82 are each cut into the shape shown in FIG. 8. Each cut segment has opposing tabs 94 and 96. These tabs are sewn together to make a tube. The opposing ends 97 and 99 of the tube are then joined together and are sewn to the frame member 16 of the face seal 10 as shown in FIG. 3. The elastic zone 90 thus resides towards the peripheral end 26 of the sealing member 18 (FIGS. 1 and 3). The nonelastic zone 20, as defined by zones of material 86 and 88, thus becomes located closer to the fixed portion of the face seal as noted by numeral 24 in FIG. 3. Not only may portions 86 and 88 contain less elastic material than portion 90, but portions 86 and 88 may also include a tighter weave so that the porosity of zone 20 as shown in FIGS. 1 and 3 has significantly less air permeability than zone 22. Zone 22 thus would be more porous and would have a lower pressure drop than zone 20. Zone 22, accordingly, would form a path of least resistance for air that is to be exhausted from the interior gas space of the supplied air helmet. The pressure drop across the face seal as a whole typically is about 10 to 200 Pascals, and more typically about 20 to 110 Pascals. The high permeability zone 22 preferably has a pressure drop of about 10 to 100 Pascals, more preferably about 20 to 70 Pascals. Low permeability zone 20 preferably has a pressure drop of about 90 to 200 Pascals across it, more preferably about 120 to 180 Pascals. The pressure drop can be measured by clamping the face seal over a 60 millimeter diameter hole using a pair of pneumatic chucks. A manometer measures the pressure on each side of the face seal using a flow rate of 85 liters per minute. The air flow rate across the materials of the face seal typically is about 5 to 200 $cm^3/s/cm^2$, and more typically about 20 to 150 $cm^3/s/cm^2$. The high permeability zone 22 preferably has an air flow rate of 85 to 200 $cm^3/s/cm^2$, more preferably about 100 to 150 $cm^3/s/cm^2$. Low permeability zone 20 preferably has an air flow rate of about 5 to 80 $cm^3/s/cm^2$ across it, more preferably about 20 to 70 $cm^3/s/cm^2$. Air flow rates can be measured using the test method described in ASTM D737-96, Standard Test Method for Air Permeability of Textile Fabrics.

Figure 10:
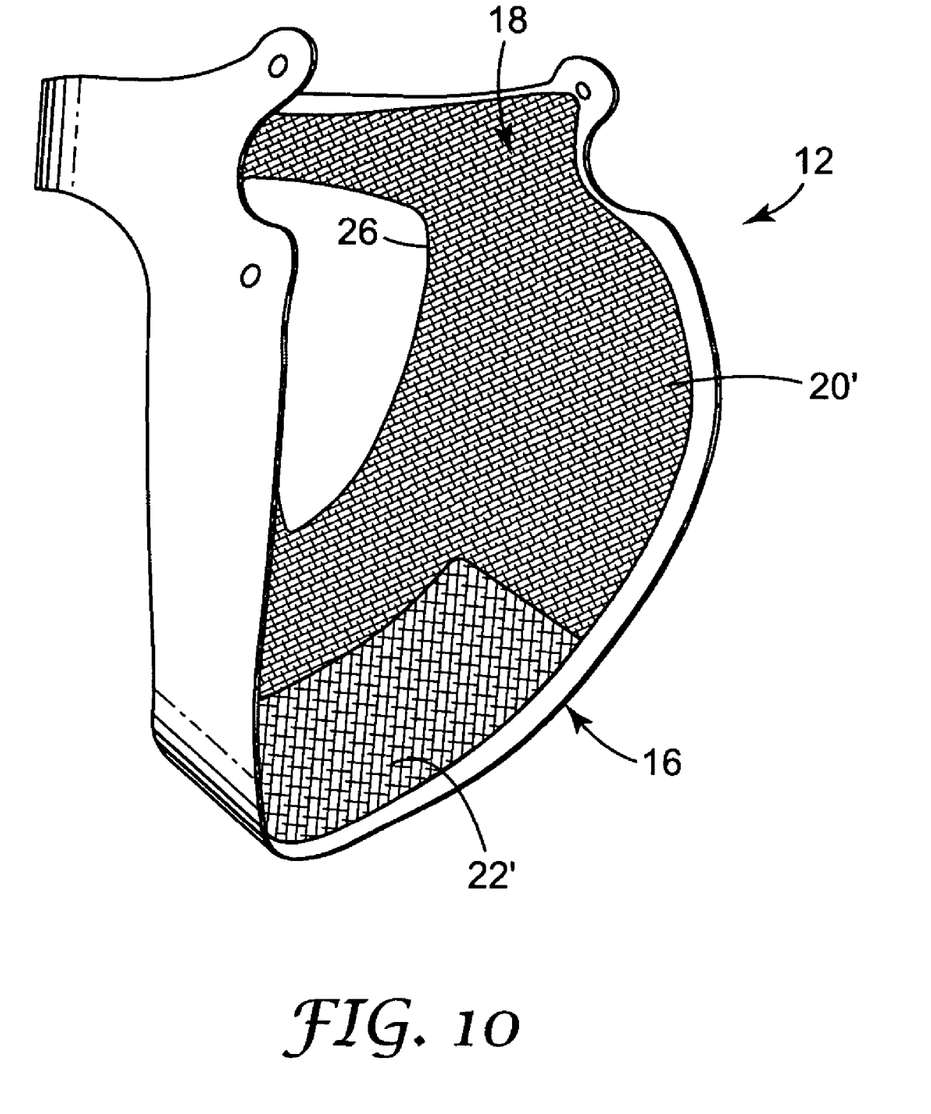
FIG. 10 is a rear perspective view of a second embodiment of a face seal 12 in accordance with the present invention.

FIG. 10 shows another embodiment of a face seal 12. Like the embodiment illustrated in the previous figures, face seal 12 includes a frame member 16 and a sealing member 18. The sealing member 18 has first and second zones of permeability 20' to 22'. Zone 22' has a greater permeability than zone 22 and is located mainly in the chin region of the wearer. The positive pressure air that is located within the interior gas space would predominantly exit the interior gas space through zone 22'. Although air would also be able to exit the sealing member 18 through zone 20', the air would be directed in general towards the chin region of the user when wearing a supplied air helmet that had the face seal illustrated in FIG. 10.

In the present invention, a controlled flow of air from the exit port 77 (FIG. 5) across the face of the wearer may be achieved. The clean air that enters the breathing zone from port 77 (FIG. 5) exits the interior gas space predominantly through the more porous zone 22, 22' (FIGS. 1, 3 and 10). Because of the increased pressure within the interior gas space, it is more difficult for contaminants to enter the breathing zone of the supplied air helmet. Sealing member zone 22, 22' being the area where air is predominantly forced out of the interior gas space assists in precluding an inadvertent influx of contaminants into that interior gas space. The higher pressure that exists within the interior gas space forces the air out of the pores that are present in zone 22, 22'. Thus, the provision of a sealing member that has a differentiated permeability or differential air flow rate, allows air to sweep across the face or breathing zone of the wearer while precluding the inadvertent influx of contaminants into the interior gas space.

As an alternative to using a face seal that has knits of different densities to provide a face seal that has differentiated permeability, it may also be possible to, for example, coat a non-porous plastic layer onto the sealing member in areas where permeability is not as desired. Alternatively, a non-porous sheet could be secured to the face seal, for example, between layers 28 and 30 as shown in FIG. 3. Further, it could be possible to use a microporous membrane that would enable air to diffuse through the membrane but preclude contaminant inflow.

In addition to the powered air systems mentioned above, the present invention also could be used in conjunction with a compressed air system such as a self-contained breathing apparatus (SCBA) that has a tank of air or oxygen, typically under pressure, for supplying clean air to a person. Examples of SCBA systems are shown in the following U.S. Pat. Nos. 6,478,025, 4,886,056, 4,586,500, and 4,437,460. For purposes of construing this invention, a compressed air system is considered to be a supplied air system. Further, the inventive supplied air systems may be used not only in conjunction with welding helmets or welding environments but may also be used, for example, in helmets fashioned for surgical environments and clean rooms—see, for example, U.S. Pat. Nos. 4,901,716, 4,055,173, 4,019,508, and 3,955,570.

The following Example has been selected merely to further illustrate features, advantages, and other details of the invention. It is to be expressly understood, however, that while the Example serves this purpose, the particular ingredients and amounts used, as well as other conditions and details, are not to be construed in a manner that would unduly limit the scope of this invention.

EXAMPLE

The face seal sealing member was made from a rectilinear 1& 1 rib knitted blank that had been cut and sewn to achieve the desired shape and configuration. The blank was made from three yarns: a combined flame-retardant/comfort yarn, an elastic yarn, and a water soluble yarn. The combined flame-retardant/comfort yarn contained Kanecaron™ fiber, Protex-M, (a modified acrylic available from the Kaneka Corporation, Japan) and cotton fiber. Relative to each other, the Kanecaron™ fiber was used at 55 weight %, and the cotton fiber was used at 45 weight %. The elastomeric yarn was 200 decitex and contained an elastane, Lycra™, and crimped nylon at 62 wt. % and 38 wt. %, respectively. These two yarns functioned as the primary structural element in the knitted blank. The combined flame-retardant/cotton yarn and the elastic yarn were both dyed blue. The flame-retardant/comfort yarn was waxed as well. Content of elastic yarn in the blank varied along the length of the blank with the highest amount of yarn in the centre of the blank, reducing to no elastic yarn at the top and bottom of the blank. To enable a series of blanks to be produced in a continuous manner, a row of water soluble yarn (Grilon™EMS-Chimie AG, Switzerland) was knitted at the end of each blank. The continuous fabric was knitted on a 16 gg (16 needles per inch or 6.3 needles/cm) power flat machine that had 620 needles in use. When subjected to steam treatment, the water-soluble yarn dissolved to form the individual blank from the continuous-length knit. The blank included five graduated areas:

Area 1 was a stiffer knit that had an extra yarn end and was designed to allow clean air to be exhausted from the headtop. It contained three ends of the Kanecaron™/cotton yarn, had 24 cycles and 48 rows. Area 2 was a transition area between the exhaust area 1 and the face seal area 3. It comprised two ends of 1/50 count yarn and 48 rows that contained tucked Lycra™ yarn, used one in every 4 rows. Area 3 was the face contact area and was designed to be comfortable against the skin. Area 3 comprises two ends of 1/50 count yarn and had 11 cycles and 88 rows, in which one in every two rows was tucked with Lycra™ yarn. Area 4 was a transition area between the face contact area and the exhaust area and had the same structure as area 2. Area 5 also was an exhaust area and had the same structure as area 1.

With a greater percentage of elastic yarn near the center of the blank, the side edges of the blank tapered or 'waisted' as the edge was followed to the center of the blank. To form the face seal of the invention, the blank edges were sewn together using a type 301 lockstitch to form a cylinder. The cylinder was then folded such that the edges of the two open ends could be sewn together, adding a type 514 four thread overlock. These edges were also sewn to a supporting plastic frame, which was a presscut 1 mm thick black polypropylene plastic. The knitted material was secured using a 301 lockstitch sewing machine that had 3–4 stitches per centimeter. Finally a leather tab was sewn to the knitted material. The resulting face seal was then used for airflow analysis.

Airflow analyses were conducted on face seal target areas in a manner that reflected the extended or stretch configuration of the seal material while the seal was fixed in a helmet. Target areas were selected by mapping zones of flow desirability (high or low). The stretched configuration of the face seal was translated to the test fixture by first marking one-inch diameter circles on target areas of the seal while it was fixed on the helmet. The face seal was then removed from the helmet and fixtured in the test apparatus so that the material of the target area was stretched into the same configuration as it had been while attached to the helmet. Testing of the seal material was conducted by the test method described in ASTMD737-96, *Standard Test Method for Air Permeability of Textile Fabrics,* using a one-inch flow orifice.

Target areas for airflow evaluation of the face seal were mapped into flow points or locations A–E. These locations represented regions on the face seal that had desirably high or low air flow characteristics. The air-flow map was designed to direct the air delivered to the helmet preferentially through certain parts of the face seal to help flush the breathing zone of the helmet while preventing inward penetration of potentially hazardous gases.

Figure 9:
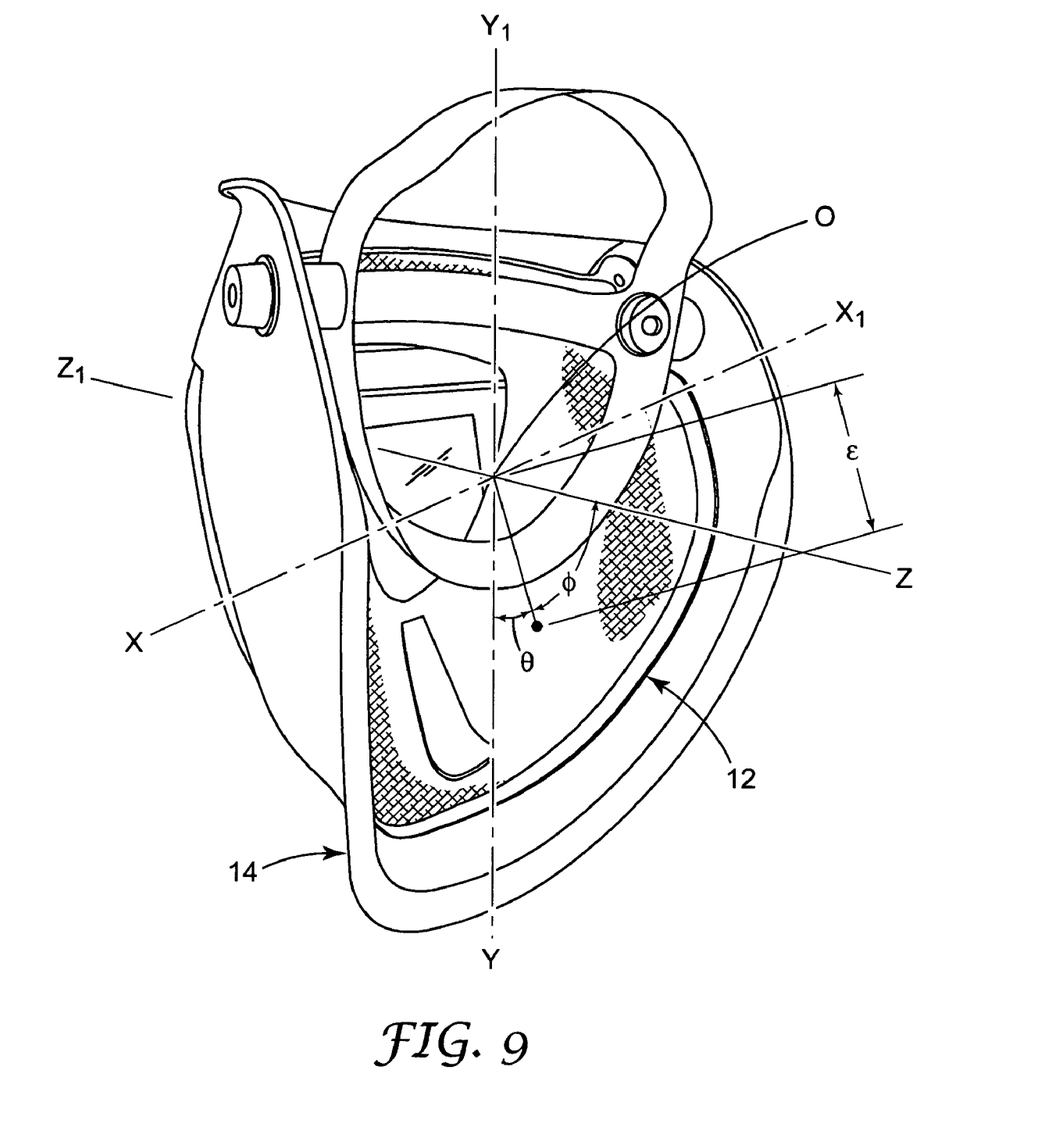
FIG. 9 is a rear perspective view of a supplied air helmet 10, in accordance with the present invention, illustrating the face seal 12 mounted to the visor 14.

Spherical coordinates were used to define the center position of the flow locations as they would generally occur with the seal placed in the helmet/seal assembly. Orientation and length of a location line, defined between an origin of a coordinate system and the center of the flow region, were used to locate the flow point. The origin of the coordinate system was located at a point, defined by the intersection of three reference lines relating to the Example helmet, as shown in FIG. 9 using designator "O". Reference line $YY_1$ bisected the helmet opening from side to side, reference line $XX_1$ was perpendicular to line $YY_1$ and roughly bisected the helmet opening from front to back. Reference line $XX_1$ additionally intersected line $ZZ_1$. Line $ZZ_1$ passed centrally through the opening of the face seal, as it was located in the helmet. Reference lines $YY_1$ and $XX_1$ lied on a plain that defined the bottom opening of the helmet; with reference line $ZZ_1$ perpendicular to both lines $YY_1$ and $XX_1$.

Orientation of the location line was indicated by spherical coordinate angles $\theta$ and $\phi$. Angle $\theta$ defined the orientation between the locating line and the line OY, with "O" being the origin point. Angle $\phi$ defined the orientation between the locating line and the line OZ. A $\theta$-defining angle that might locate the chin of a wearer would be in the 0 degree range, with a $\theta$-defining angle locating a position to the side of a wearers head being closer to 90 degrees. A $\phi$-defining angle close to 110 degrees would give the location of the chin area of the face seal, with a $\phi$-defining angle close to 160 degrees giving the approximate location of the forehead contacting area of the face seal. The length, $\epsilon$, of the location line is the length of the line from the origin to the center of the flow zone. For the helmet evaluated in the Example, the distance from the front of the helmet to the line $XX_1$ was 15 centimeters with the distance from the side of the helmet to line $YY_1$ being 11 centimeters.

The airflow map and the airflow values are set forth in Table 1:

TABLE 1

| Location | Air Flow | | | Hemispherical Coordinates | | |
|---|---|---|---|---|---|---|
| | Flow Desired | Rate ($cm^3/s/cm^2$) | General Location | θ (degrees) | φ (degrees) | ε (cm) |
| A | Low | 56 | Forward of ear | 95 | 120 | 10 |
| B | High | 116 | Temple | 140 | 135 | 14 |
| C | Low | 63 | Forehead | 180 | 160 | 22 |
| D | High | 147 | Lower chin | 0 | 125 | 9 |
| E | Low | 61 | Upper chin | 0 | 107 | 11 |

As is seen in Table 1, airflow maps can be designed to specific flow zones in a face seal. By mapping the airflow through the face seal in this way, the volumetric flow delivered to the helmet can be optimally utilized to purge the protective system while maintaining sufficient resistance to in-flow of hazardous gases.

This invention may take on various modifications and alterations without departing from the spirit and scope thereof. Accordingly, it is to be understood that this invention is not to be limited to the above-described, but it is to be controlled by the limitations set forth in the following claims and any equivalents thereof.

It is also to be understood that this invention may be suitably practiced in the absence of any element not specifically disclosed herein.

All patents and patent applications cited above, including those in the Background section, are incorporated by reference into this document in total.

What is claimed is:

1. A supplied air helmet that comprises:
   (a) a visor; and
   (b) a face seal that is secured to the visor and that includes a sealing member and a frame member, wherein the sealing member extends radially inward from the frame member and the sealing member has at least first and second zones of permeability, and wherein the second zone has greater permeability than the first zone.

2. The supplied air helmet of claim 1, wherein the second zone is located on the sealing member in the vicinity of the wearer's chin when the helmet is worn.

3. The supplied air helmet of claim 1, wherein the sealing member comprises a fabric that includes an elastic yarn and that has a greater percentage of elastic yarn in the second zone than in the first zone.

4. The supplied air helmet of claim 3, wherein the second zone contains about 2 to 10% elastic yarn based on the fabric weight.

5. The supplied air helmet of claim 1, wherein the frame member is integral to the visor.

6. The supplied air helmet of claim 1, wherein the frame member is not integral to the visor and is removably attached thereto.

7. The supplied air helmet of claim 1, wherein the sealing member comprises a knitted fabric, and wherein the knitted fabric includes an elastic yarn, there being more elastic yarn present in the second zone than in the first zone.

8. The supplied air helmet of claim 1, wherein the sealing member comprises a fabric that has a fold that defines an inner peripheral edge of the sealing member.

9. The supplied air helmet of claim 1, being a welding helmet.

10. The welding helmet of claim 9, wherein clean air is supplied to the welding helmet from a powered air purifying respirator.

11. The supplied air helmet of claim 1, wherein the second zone has greater elasticity than the first zone.

12. The supplied air helmet of claim 1, wherein the second zone exhibits a pressure drop of about 10 to 200 Pascals, and wherein the first zone exhibits a pressure drop of about 9 to 200 Pascals.

13. The supplied air helmet of claim 12, wherein the second zone exhibits a pressure drop of about 20 to 70 Pascals and the first zone exhibits a pressure drop of about 120 to 180 Pascals.

14. The supplied air helmet of claim 1, wherein the flow rate of the second zone is about 85 to 200 $cm^3/s/cm^2$ and the flow rate of the first zone is about 5 to 80 $cm^3/s/cm^2$ when tested in accordance with ASTM 737-96.

15. The supplied air helmet of claim 14, wherein the flow rate of the second zone is about 100 to 150 $cm^3/s/cm^2$ and the flow rate of the first zone is about 20 to 70 $cm^3/s/cm^2$.

16. The supplied air helmet of claim 1, wherein the zone 1 has a plastic material coated thereon.

17. A supplied air helmet that comprises:
   (a) a visor; and
   (b) a face seal that is secured to the visor and that includes a sealing member that extends therefrom, the sealing member including a fabric that has first and second zones of permeability, wherein the second zone has a greater permeability than the first zone, the fabric having a folded edge that defines an inner periphery of the sealing member, wherein the flow rate of the second zone is about 85 to 200 $cm^3/5/cm^2$ and the flow rate of the first zone is about 5 to 80 $cm^3/5/cm^2$.

18. A welding helmet that comprises:
   (a) a visor; and
   (b) a face seal that is secured to the visor and that includes a sealing member that extends therefrom, the sealing member including a fabric that has first and second zones of permeability, wherein the second zone has a greater permeability than the first zone, the fabric having a folded edge that defines an inner periphery of the sealing member, wherein the flow rate of the second zone is about 85 to 200 $cm^3/5/cm^2$ and the flow rate of the first zone is about 5 to 80 $cm^3/5/cm^2$.

* * * * *

UNITED STATES PATENT AND TRADEMARK OFFICE
CERTIFICATE OF CORRECTION

PATENT NO. : 7,197,774 B2
APPLICATION NO. : 10/987512
DATED : April 3, 2007
INVENTOR(S) : Desmond T. Curran It is certified that error appears in the above-identified patent and that said Letters Patent is hereby corrected as shown below:

Column 5
Line 55, delete "polycarylonitriles," and insert -- polyacrylonitriles, --, therefor.

Column 10
Line 23, delete "Standard Test.......Fabrics." and insert the same on Line 21 as a continuation of the paragraph.

Column 11
Line 13, after "Nos." insert -- : --.

Column 14
Line 46, in claim 17, delete "200 $cm^3/5/cm^2$" and insert -- 200 $cm^3/s/cm^2$ --, therefor.
Line 47, in Claim 17, delete "80 $cm^3/5/cm^2$." and insert -- 80 $cm^3/s/cm^2$. --, therefor.
Line 57, in Claim 18, delete "200 $cm^3/5/cm^2$" and insert -- 200 $cm^3/s/cm^2$ --, therefor.
Line 58, in Claim 18, delete "80 $cm^3/5/cm^2$." and insert -- 80 $cm^3/s/cm^2$. --, therefor.

Signed and Sealed this

Twenty-sixth Day of June, 2007

JON W. DUDAS
*Director of the United States Patent and Trademark Office*